US012657768B2

(12) United States Patent
Dou et al.

(10) Patent No.: US 12,657,768 B2
(45) Date of Patent: Jun. 16, 2026

(54) METHODS AND SYSTEMS FOR POSITIONING IN AN MEDICAL PROCEDURE

(71) Applicant: SHANGHAI UNITED IMAGING HEALTHCARE CO., LTD., Shanghai (CN)

(72) Inventors: Shidan Dou, Shanghai (CN); Xiaofen Zhao, Shanghai (CN); Leimin Shang, Shanghai (CN); Yanfeng Du, Shanghai (CN)

(73) Assignee: SHANGHAI UNITED IMAGING HEALTHCARE CO., LTD., Shanghai (CN)

( * ) Notice: Subject to any disclaimer, the term of this patent is extended or adjusted under 35 U.S.C. 154(b) by 384 days.

(21) Appl. No.: 18/336,998

(22) Filed: Jun. 17, 2023

(65) Prior Publication Data

US 2023/0334698 A1 Oct. 19, 2023

Related U.S. Application Data

(63) Continuation of application No. PCT/CN2021/123459, filed on Oct. 13, 2021.

(30) Foreign Application Priority Data

Dec. 17, 2020 (CN) .......................... 202011500980.3

(51) Int. Cl.
G06T 7/73 (2017.01)
G06T 3/40 (2024.01)
(Continued)

(52) U.S. Cl.
CPC ................. G06T 7/75 (2017.01); G06T 3/40 (2013.01); G06T 7/11 (2017.01); G06V 10/22 (2022.01);
(Continued)

(58) Field of Classification Search
CPC ......... G06T 7/0014; G06T 2207/20081; G06T 2207/30004; G06T 2207/20104;
(Continued)

(56) References Cited

U.S. PATENT DOCUMENTS

| | | | |
|---|---|---|---|
| 10,482,603 B1 | 11/2019 | Fu et al. | |
| 2010/0284590 A1* | 11/2010 | Peng | G06T 7/12 |
| | | | 382/128 |

(Continued)

FOREIGN PATENT DOCUMENTS

| | | |
|---|---|---|
| CN | 108846828 A | 11/2018 |
| CN | 110223352 A | 9/2019 |

(Continued)

OTHER PUBLICATIONS

Y. Zhan, M. Dewan, M. Harder, A. Krishnan and X. S. Zhou, "Robust Automatic Knee MR Slice Positioning Through Redundant and Hierarchical Anatomy Detection," in IEEE Transactions on Medical Imaging, vol. 30, No. 12, pp. 2087-2100, Dec. 2011 (Year: 2011).*

(Continued)

*Primary Examiner* — Sumati Lefkowitz
*Assistant Examiner* — Aaron Joseph Sorrin
(74) *Attorney, Agent, or Firm* — METIS IP LLC

(57) ABSTRACT

The present disclosure discloses a method for positioning. The method may include obtaining a scout image of a target object and inputting the scout image of the target object into a positioning model. The method may also include determining a positioning frame in the scout image based on an output result of the positioning model. The positioning model may be obtained by training based on training scout images and information of the gold standard positioning frames. Each of the gold standard positioning frames may be (Continued)

400 obtaining a scout image of a target object ⟋210 inputting the scout image of the target object into a positioning model, and determining at least one positioning frame in the scout image based on an output result of the positioning model, the positioning model including a region generation sub-network and a target classification sub-network, the region generation sub-network being used to generate the positioning frame corresponding to each of the at least one portion in the scout image, and the target classification sub-network being used to determine scanning portion information corresponding to the positioning frame ⟋220

Obtaining a scanning protocol of the target, and determining a target positioning frame from the at least one positioning frame corresponding the at least one portion according to a target scanning portion in the scanning protocol ⟋230 in, from, or determined based on one of the training scout images and used for scanning.

20 Claims, 6 Drawing Sheets

(51) Int. Cl.

| | |
|---|---|
| *G06T 7/11* | (2017.01) |
| *G06V 10/22* | (2022.01) |
| *G06V 10/764* | (2022.01) |
| *G06V 10/774* | (2022.01) |
| *G06V 20/50* | (2022.01) |
| *G16H 70/20* | (2018.01) |

(52) U.S. Cl.
CPC .......... *G06V 10/764* (2022.01); *G06V 10/774* (2022.01); *G06V 20/50* (2022.01); *G06T 2207/20081* (2013.01); *G06T 2207/30004* (2013.01); *G06V 2201/03* (2022.01); *G16H 70/20* (2018.01)

(58) Field of Classification Search
CPC .. G06T 7/11; G06T 7/75; A61B 6/488; G06V 10/25; G06V 10/22; G06V 2201/03; G06V 10/26; G06V 10/82; G16H 50/70; G16H 30/20; G16H 30/40; G06N 3/08
See application file for complete search history.

(56) References Cited

U.S. PATENT DOCUMENTS

| | | | |
|---|---|---|---|
| 2015/0043774 A1* | 2/2015 | Harder ................. | G06V 10/141 |
| | | | 382/128 |
| 2019/0320934 A1* | 10/2019 | Odry .................... | A61B 5/7264 |
| 2020/0012895 A1 | 1/2020 | Zhao et al. | |
| 2021/0019890 A1* | 1/2021 | Chen ........................ | G06T 7/11 |

FOREIGN PATENT DOCUMENTS

| | | | |
|---|---|---|---|
| CN | 111028246 A | 4/2020 | |
| CN | 111275699 A | 6/2020 | |
| CN | 111340816 A | 6/2020 | |
| CN | 111724401 A | 9/2020 | |
| CN | 112530554 A | 3/2021 | |
| WO | WO-2019169251 A1 * | 9/2019 | ............. G06T 7/174 |

OTHER PUBLICATIONS

International Search Report in PCT/CN2021/123459 mailed on Jan. 13, 2022, 5 pages.
Written Opinion in PCT/CN2021/123459 mailed on Jan. 13, 2022, 9 pages.
First Office Action in Chinese Application No. 202011500980.3 mailed on Jul. 21, 2022, 18 pages.

* cited by examiner

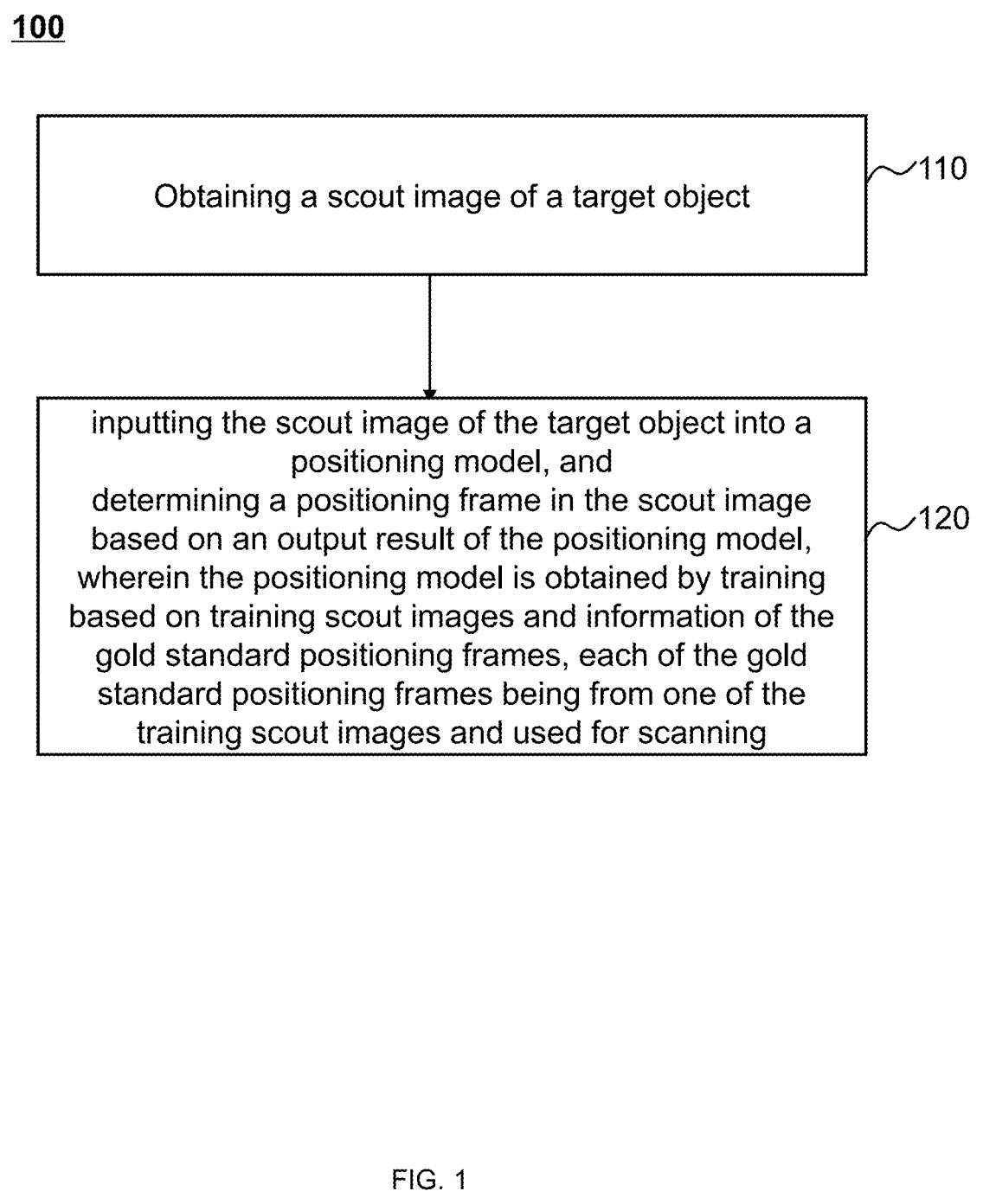

100

Obtaining a scout image of a target object                    ⌇110 inputting the scout image of the target object into a
positioning model, and
determining a positioning frame in the scout image
based on an output result of the positioning model,        ⌇120
wherein the positioning model is obtained by training
based on training scout images and information of the
gold standard positioning frames, each of the gold
standard positioning frames being from one of the
training scout images and used for scanning

FIG. 1

Positioning frame                                    Mask area

<u>400</u>

```
┌─────────────────────────────────────────────────────────┐
│        obtaining a scout image of a target object         │  ⌇210
└─────────────────────────────────────────────────────────┘
                              │
                              ▼
┌─────────────────────────────────────────────────────────┐
│     inputting the scout image of the target object into a │
│                     positioning model, and                │
│     determining at least one positioning frame in the scout│
│     image based on an output result of the positioning model,│
│     the positioning model including a region generation sub-│
│       network and a target classification sub-network, the │  ⌇220
│     region generation sub-network being used to generate the│
│      positioning frame corresponding to each of the at least│
│          one portion in the scout image, and the target    │
│         classification sub-network being used to determine │
│         scanning portion information corresponding to the  │
│                      positioning frame                     │
└─────────────────────────────────────────────────────────┘
                              │
                              ▼
┌─────────────────────────────────────────────────────────┐
│       Obtaining a scanning protocol of the target, and     │
│     determining a target positioning frame from the at least│
│      one positioning frame corresponding the at least one  │  ⌇230
│        portion according to a target scanning portion in the│
│                      scanning protocol                     │
└─────────────────────────────────────────────────────────┘
```

FIG. 4

Positioning frame 1

Positioning frame 2

METHODS AND SYSTEMS FOR POSITIONING IN AN MEDICAL PROCEDURE

CROSS-REFERENCE TO RELATED APPLICATION

This application is a continuation of International Patent Application No. PCT/CN2021/123459, filed on Oct. 13, 2021, which claims priority of Chinese Patent Application No. 202011500980.3 filled on Dec. 17, 2020, the contents of which are entirely incorporated herein by reference.

TECHNICAL FIELD

The present disclosure relates to deep learning, and in particular to a method, system for positioning in a medical procedure.

BACKGROUND

Medical scanning technology may be used on various portions of a human body and plays a vital role in diseases, treatment progress, etc. In various medical scanning techniques, a positioning frame for scanning needs to be determined before scanning the human body.

An existing positioning frame may be generally determined by a manual operation. For example, a starting line, an ending line, and a range in a scout image may be selected through a tool such as a keyboard or a mouse. The manual operation mode has a great workload and requires a high ability of an operator.

SUMMARY

The present disclosure provides a method, a system, a storage medium, and an electronic device for positioning, to quickly and accurately determine a positioning frame.

In a first aspect, the present invention provides a method for positioning. The method may include obtaining a scout image of the target object and inputting the scout image of the target object into a pre-positioning model. The method may also include determining a positioning frame in the scout image based on an output result of the positioning model. The positioning model may be obtained by training based on training scout images and information of the gold standard positioning frames. Each of the gold standard positioning frames may be from or determined based on one of the training scout images and used for scanning.

In some embodiments, the positioning model may include a segmentation model. The determining the positioning frame in the scout image based on the output result of the positioning model may include: obtaining a segmentation result output by the segmentation model and determining an outline of a segmented region in the segmentation result as the positioning frame.

In some embodiments, the segmentation model may include an encoding module and a decoding module. The encoding module may include sequentially connected down-sampling network layers, and the decoding module may include sequentially connected up-sampling network layers, an end down-sampling network layer in the encoding module may be connected to an initial up-sampling network layer in the decoding module, and the down-sampling network layer and the up-sampling network layer in the encoding module and the decoding module of the same scale may be horizontally connected.

In some embodiments, a training process of the segmentation model may include: obtaining the training scout images and the information of the gold standard positioning frames; generating a gold standard mask region of one of the training scout images based on the information of a gold standard positioning frame corresponding to the training scout image; and iteratively training, based on the training scout images and gold standard mask regions corresponding to the training scout images, a preliminary segmentation model, and obtaining the segmentation model.

In some embodiments, the method may further include: identifying at least one portion of the target object in the scout image; and respectively calling, based on the at least one portion of the target object, the positioning model corresponding to each of the at least one portion. The positioning model corresponding to each of the at least one portion may be used to determine the positioning frame corresponding to the each of the at least one portion.

In some embodiments, the positioning model may include a region generation sub-network and a target classification sub-network. The region generation sub-network may be used to generate the positioning frame corresponding to each of the at least one portion in the scout image, and the target classification sub-network may be used to determine scanning portion information corresponding to the positioning frame.

In some embodiments, the method may further include: obtaining a scanning protocol of the target object; and determining a target positioning frame from each of at least one positioning frame corresponding to the at least one portion according to a target scanning portion in the scanning protocol.

In a second aspect, the present invention also provides a system for positioning. The system may include a scout image obtaining module configured to obtain a scout image of a target object; a positioning frame determination module configured to input the scout image of the target object into a positioning model, and determine a positioning frame in the scout image based on an output result of the positioning model. The positioning model may be obtained by training based on training scout images and information of the gold standard positioning frames. Each of the gold standard positioning frames may be in, from, or determined based on one of the training scout images and used for scanning.

In a third aspect, the present disclosure also provides an electronic device. The an electronic device may include one or more processors; a memory configured to store one or more programs; when the one or more programs are executed by the one or more processors, the one or more processors may be made to implement the positioning process.

In a fourth aspect, the present disclosure also provides a non-transitory storage medium storing a computer program, the computer program including program instructions. When the program instructions are executed by a processor, the processor executes the positioning method.

In the technical solution provided by the embodiment of the present disclosure, a scout image of a target object may be processed through a preset positioning model, and positioning frame information for scanning the target object may be output. Without any subsequent processing of the obtained positioning frame information, an efficiency, and an accuracy of determining the positioning frame information may be improved.

BRIEF DESCRIPTION OF THE DRAWINGS

FIG. 1 is a schematic flowchart illustrating a positioning process according to some embodiments of the present disclosure;

FIG. 4 is a schematic flowchart illustrating a positioning process according to the embodiments of the present disclosure;

DETAILED DESCRIPTION

Figure 2:
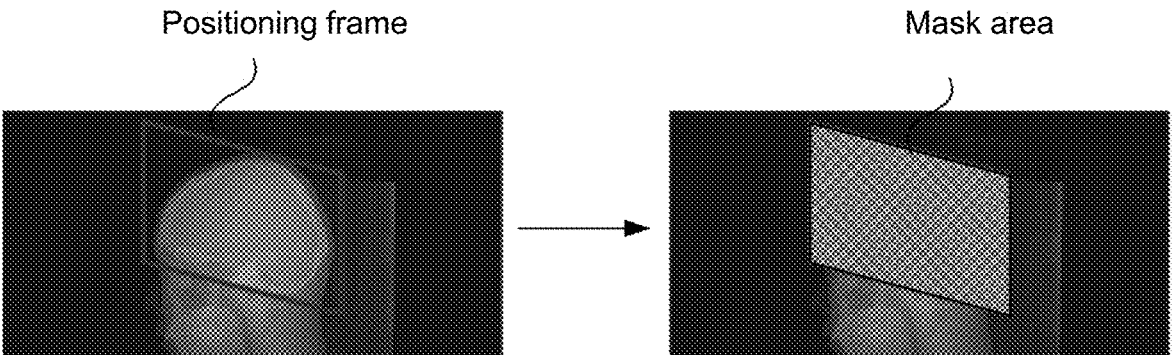
FIG. 2 is a schematic diagram illustrating a conversion process of a positioning frame according to the embodiments of the present disclosure.

The present disclosure will be further described in detail below in conjunction with the accompanying drawings and embodiments. It should be understood that the specific embodiments described here are only used to explain the present disclosure, but not to limit the present disclosure. In addition, it should be noted that, for the convenience of description, only a portion of structures related to the present disclosure are shown in the drawings.

FIG. 1 is a schematic flowchart illustrating an exemplary process for positioning in a medical procedure according to some embodiments of the present disclosure. Process 100 may be applicable to the situation where the positioning frame is automatically determined before scanning the target object. Process 100 may be performed by a positioning device provided by some embodiments of the present disclosure. The positioning device may be integrated into an electronic device such as a computer or a scanning device. Process 100 may specifically include the following operations.

In 110, a scout image of a target object may be obtained.

In 120, the scout image of the target object may be input into a positioning model.

The target object may be an object to be scanned, and the object may be a human body, an animal body, or a partial region of a human body or an animal body. A scan to be performed may be a single modality scan, such as a computed tomography (CT) scan, a magnetic resonance imaging (MRI) scan, a positron emission computed tomography (PET) scan, an X-ray film scan, an ultrasound image scan, or a multi-modality scan, such as a combination of multiple modes scan.

The scout image may be an image of the target object for positioning before scanning. The scout image may present at least a portion of the target object to be scanned. In some embodiments, the scout image may include two or more than two portions of the target object. The scout image may be obtained before scanning the target object. In some embodiments, the scout image may be a previous scanning image of the same modality as or a different modality from the current scan of the target object. In some embodiments, the scout image may include an optical photographic image of the target object.

The scout image of the target object may be processed through the positioning model to obtain a positioning result of the scanning of the target object. The positioning frame may be in a shape of a rectangle, a polygon, or an irregular shape, etc. The positioning result may include the positioning frame drawn in the scout image, and/or include description information of the positioning frame. The description information may include the size and the range of the positioning frame. For example, the description information may include vertex coordinates, center coordinates, and width and height information of the positioning frame.

In some embodiments, the positioning model may be a machine learning model such as a neural network model. The positioning model may be obtained through an end-to-end training mode. Specifically, the positioning model may be obtained by training based on training scout images and information of the gold standard positioning frames. Each of the gold standard positioning frames may be in, from, or determined based on one of the training scout images and used for scanning. The information of the gold standard positioning frames used for scanning may be drawn by experienced scanning technicians, and the gold standard positioning frame information may be scanned directly without any post-processing process. The information of the gold standard positioning frames may be the positioning frame drawing records of the technicians in actual use. In some embodiments, the information of the gold standard positioning frame may be historical data (e.g., a historical positioning frame) selected according to current scan information for the target object. For example, a historical positioning frame used for scanning a subject that is the same patient as the target subject may be selected as the gold standard positioning frame. As another example, a historical positioning frame used for scanning a subject by a scanning device that is the same modality as the scanning device for scanning the target subject may be selected as the gold standard positioning frame. As still another example, a historical positioning frame used for scanning a subject and determined by a technician that is the same as the technician for scanning the target subject may be selected as the gold standard positioning frame. As still another example, a historical positioning frame used for scanning a subject by a scanning device that has at least one parameter same as the scanning device for scanning the target subject may be selected as the gold standard positioning frame. As still another example, a historical positioning frame used for scanning a subject based on a scanning protocol that has at least one parameter same as a parameter of the scanning protocol for scanning the target subject may be selected as the gold standard positioning frame.

Correspondingly, based on the above-mentioned information of the gold standard positioning frames used for scanning and the training scout images, the positioning model may be used to output positioning frame information that may be directly used to scan the target object without any further post-processing. In this way, the process of determining the positioning frame may be simplified, the accuracy of the positioning frame may be improved, and the experience requirement for the scanning technicians may be lowered.

In some embodiments, the positioning model may include a segmentation model. The segmentation model may be used to segment the positioning frame from the scout image. Inputting a scanned image (e.g., the scout image) of the target object into the segmentation model to obtain a segmented positioning frame output by the segmentation model, that is, a segmentation result. Correspondingly, the determining a positioning frame in the scout image based on an output result of the positioning model may include obtaining a segmentation result outputted by the positioning model and determining an outline of a segmented region in the segmentation result as the positioning frame.

The training process of the positioning frame segmentation model may include obtaining training scout images and information of the gold standard positioning frames each of which is presented in one of the training scout images and used for scanning. The training process may also include for one of the training scout images, determining a mask region in the training scout image based on the information of the gold standard positioning frame in the training scout image.

In some embodiments, process 100 may include determining a scanning region for the target object based on the positioning frame and causing a scanning device to perform a scan on the target object according to the scanning region. The scanning device may include a computer tomography (CT) scanner, a positron emission tomography (PET) scanner, an X-ray scanner, etc. In some embodiments, the scanning region may be a region of the target object enclosed by the positioning frame. In some embodiments, the scanning region may be a scanning range in a coordinate system of the scanning device. The scanning region in the coordinate system may be determined based on the position of the positioning frame in the scout image. For example, the position of the positioning frame in the scout image may be converted into the position of the scanning region in the coordinate system of the scanning device based on a transformation relationship between the coordinate system of the scanning device and a coordinate system of the scout image.

In some embodiments, process 100 may include determining a region of interest (ROI) based on the positioning frame. For example, an initial position of the ROI may be determined based on the positioning frame. Further, the ROI may be a region enclosed by the positioning frame. Then an accurate position of the ROI may be further determined from the region defined by the positioning frame. In some embodiments, the ROI may include a sensitive organ region (e.g., a focus, a disease-prone area, etc.). Process 100 may also include performing dose modulation for the ROI. In some embodiments, the ROI may include a motion region. Process 100 may also include performing artifact monitoring for the ROI. For example, process 100 may obtain image data of the ROI and determining whether the ROI in the image region includes artifact.

FIG. 2 is a diagram illustrating a conversation process of the positioning frame in the training of a positioning model according to some embodiments of the present disclosure. The left image in FIG. 2 is a scout image including the information of a gold standard positioning frame. The information of the gold standard positioning frame may be a head positioning frame drawn by a technician. The right image in FIG. 2 is the scout image including a mask region. The mask region is encompassed in the gold standard positioning frame. The preliminary segmentation model may be iteratively trained based on a great number of training scout images and the gold standard mask regions corresponding to the training scout images, to obtain the segmentation model based on a positioning frame segmentation function.

Specifically, an iterative training may be performed on the preliminary segmentation model until a prediction segmentation region output by the segmentation model meets a preset segmentation accuracy. The iterative training may include a plurality of iterations. In each iteration, a training scout image may be inputted into the preliminary segmentation model and a prediction segmentation region may be obtained. A loss function may be determined based on the prediction segmentation region and the gold standard mask region corresponding to the training scout image. Network parameters of the segmentation model may be adjusted according to the loss function. The network parameters to be adjusted may include weight parameters in the segmentation model. The loss function during the training process may be a diss loss function, or other loss functions set according to requirements.

In some embodiments, a loss function D may be denoted as following Equation (1):

$$D = \frac{2\sum_i^n p_i g_i}{\sum_i^n p_i^2 + \sum_i^n g_i^2}, \tag{1}$$

where an prediction segmentation region P and a gold standard mask region G respectively include N pixel points, i indicates an identification of the pixel point, and $p_i$ indicates a pixel value of the i-th pixel in the prediction segmentation region P, $g_i$ indicates the pixel value of the i-th pixel in the gold standard mask region G, and, $p_i \in P$, $g_i \in G$. The diss loss function may clear an "activated" position in a non-target region in the prediction result (i.e., a segmentation result), and punish a low confidence position in the target region, thereby effectively solving a problem of unbalanced region contrast between the background and foreground (i.e., the gold standard mask region) in a medical image. The target region may also be referred to as a prediction segmentation region or a region where the prediction positioning frame is located.

Correspondingly, based on the segmentation model trained in the above process, the segmentation result obtained by processing the target object during the application process may be as the mask region in the right image of FIG. 2, and through a reverse process on the mask region, information of a positioning frame (also referred to as positioning frame information) in the left image of FIG. 2 may be obtained. For example, the positioning frame information may be boundary information of an extracted mask region, such as boundary coordinate information or boundary vertex coordinates, etc. As another example, the positioning frame information may be the information obtained by performing an edge detection to obtain the boundary of the positioning frame, and then obtaining the positioning frame information including the boundary information.

Figure 3:
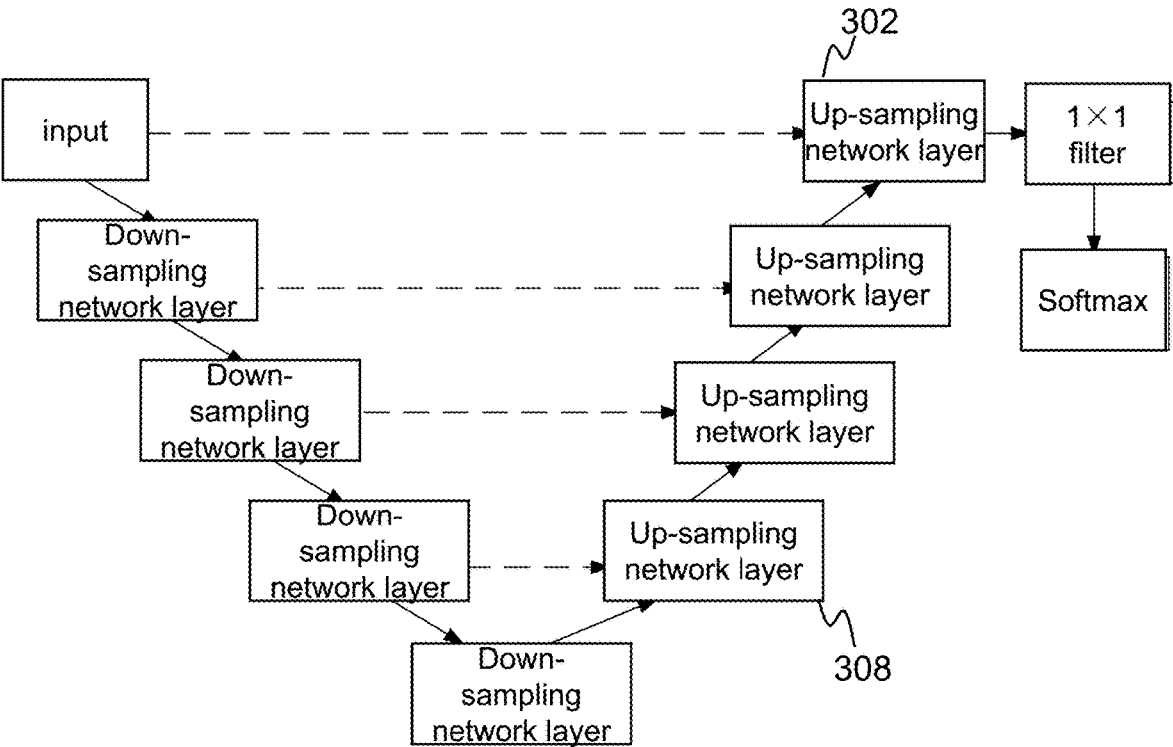
FIG. 3 is a schematic diagram illustrating a structure of a segmentation model according to the embodiments of the present disclosure.

In some embodiments, the segmentation model may include an encoding module (also referred to as an encoding sub-model) and a decoding module (also referred to as a decoding sub-model). For example, FIG. 3 is a schematic diagram illustrating a segmentation model according to the embodiments of the present disclosure. The encoding module may include sequentially connected down-sampling network layers, and the decoding module may include sequentially connected up-sampling network layers, an end down-sampling network layer in the encoding module is connected to an initial up-sampling network layer in the decoding module, and the down-sampling network layer and the up-sampling network layer in the encoding module and the decoding module on the same level are horizontally connected. As used herein, a down-sampling network layer and an up-sampling network layer refers to two network layers that process image features in the same size. The down-sampling network layer may include at least one convolutional layer. In some embodiments, each down-sampling network layer may be a convolutional block. The convolutional block may include a plurality of convolutional layers, for example, the convolutional block may be a residual block. Through the plurality of down-sampling network layers, input information may be sequentially extracted, and a spatial scale may be gradually reduced to obtain image features of different scales. The image features may form a feature image. The up-sampling network layer in the decoding module may include at least one deconvolution layer. For example, the up-sampling network layer may be a deconvolution block. Each up-sampling network layer in the decoding module recovers, through a deconvolution operation, target details and the spatial scales of the image features (or the feature image) obtained from the encoding module. At the same time, through the horizontal connection (denoted by dotted lines in FIG. 3) between the down-sampling network layer and the up-sampling network layer of the same scale, a feature image output by the down-sampling network layer may be horizontally output to the corresponding up-sampling network layer, and the output in a shallow network layer (e.g., up-sampling network layer 302) and the output of a deep network layer (e.g., up-sampling network layer 308) are combined, so that the network may consider both shallow layer information (accurate position information) and deep layer information (semantic information of the image) at the final output, so as to improve the segmentation accuracy of the segmentation model.

According to the present disclosure, a scout image of a target object may be processed through a positioning model, and positioning frame information for scanning the target object may be output. Without any subsequent processing of the obtained positioning frame information, the efficiency, and the accuracy of determining the positioning frame information are improved.

In some embodiments, different portions of the target object may correspond to different positioning models. In some embodiments, different scan types (including but not limited to a CT scan, an MR scan, a PER/CT scan, etc.) of the target object may correspond to different positioning models. In some embodiments, for one scan type (including but not limited to a CT scan, an MR scan, a PER/CT scan, etc.), different portions of the target object may correspond to different positioning models. In some embodiments, different scanning protocols and historical records may correspond to different positioning models. In some embodiments, for one scan type (including but not limited to a CT scan, an MR scan, a PER/CT scan, etc.) and a specific portion of the target subject, different scanning protocols may correspond to different positioning models. For example, for the CT scan, the positioning models corresponding to portions such as a human head, an upper abdomen of the human body, a lower abdomen of the human body, and legs may be trained respectively. A positioning model corresponding to a specific portion may be used to determine a positioning frame in the scout images of the specific portion. As another example, for the MR scan, a plurality of positioning models may be trained for the same portion for different scanning protocols, such as a T1 scanning protocol and a T2 scanning protocol. As still another example, different positioning models may be trained for each of the at least one technician, each of the at least one patient, or each of the at least one type of patient. One type of patient may have one or more of the same medical information, such as a height, a weight, an age, a gender, a disease, etc.

In some embodiments, process 100 may further include identifying at least one portion of the target object in the scout image. For example, the scout image may include only one portion, such as the head, or include two or more portions, such as the upper abdomen and the lower abdomen. The identifying at least one portion of the target object in the scout image may include comparing an image outline in the scout image with preset feature information of each of the at least one portion to determine the portion included in the scout image. By training the plurality of positioning models corresponding to different portions of the target object, a scout image of each of the at least one portion may be processed in a targeted manner (i.e., using the corresponding positioning model), thereby improving the determination accuracy of the positioning frame information.

Inn some embodiments, after determining at least one portion in the scout image, process 100 may include obtaining the scan type in the scan protocol of the at least one portion, and respectively calling, based on the at least one portion of the target object, a positioning model corresponding to the scan type and the at least one portion.

Correspondingly, inputting the scout image of the target object into the positioning model may include respectively calling the positioning model corresponding to each of the at least one of the at least one portion based on the at least one portion of the target object, and determining the positioning frame of each of the at least one of the at least one portion based on an output result of the positioning model corresponding to each of the at least one of the at least one portion. For example, when the scout image includes at least two portions, the positioning model corresponding to each of the at least two portions may be called at the same time, and the positioning frame corresponding to each of the at least two portions may be obtained based on the positioning model corresponding to one of at least two portions. By determining the positioning frame information for a plurality of portions in the scout image, it may be convenient for the operator to select, so as to avoid the situation where positioning frame is determined incorrectly due to an omission of portions.

In some embodiments, process 100 may further include obtaining the scanning protocol of the target object, and determining a target positioning frame from each of the at least one positioning frame corresponding to the at least one portion according to a scanning portion in the scanning protocol. The scanning protocol may include the portion to be scanned, and the target positioning frame may be selected from the positioning frames corresponding to the plurality of portions based on the portion to be scanned in the scanning protocol.

In some embodiments, process 100 may further include obtaining the scanning protocol of the target object, calling the positioning model corresponding to the scanning portion according to the scanning portion in the scanning protocol, and identifying the positioning frame information in the scout image based on the positioning model.

In some embodiments, process 100 may further include obtaining the scanning protocol of the target object, and calling the corresponding positioning model according to the scan type and a scan portion in the scanning protocol.

FIG. 4 is a schematic flowchart illustrating an exemplary process 400 for positioning according to the embodiments of the present disclosure. On the basis of the embodiments, a structure of a positioning model may be provided.

In 210, a scout image of a target object may be obtained.

In 220, the scout image of the target object may be input into the positioning model, and at least one positioning frame in the scout image may be determined based on an output result of the positioning model. The positioning model may include a region generation sub-network and a target classification sub-network. The region generation sub-network may be used to generate the positioning frame corresponding to each of the at least one portion in the scout image, and the target classification sub-network may be used to determine information of a scanning portion corresponding to the positioning frame. A scanning portion corresponding to the positioning frame refers to a portion defined or limited by the positioning frame.

In 230, a scanning protocol of the target object may be obtained, and a target positioning frame may be determined from the at least one positioning frame corresponding to the at least one portion according to a target scanning portion in the scanning protocol. In some embodiments, in 220, multiple positioning frames may be determined from the scout image. Each of the multiple positioning frames may correspond to one of multiple portions of the target object in the scout image. The target positioning frame may be determined from the multiple positioning frames based on the target scanning portion in the scanning protocol. One of the multiple portions of the target object that is the same as the target scanning portion may be determined and the positioning frame corresponding to the one of the multiple portions may be designated as the target positioning frame.

Figure 5:
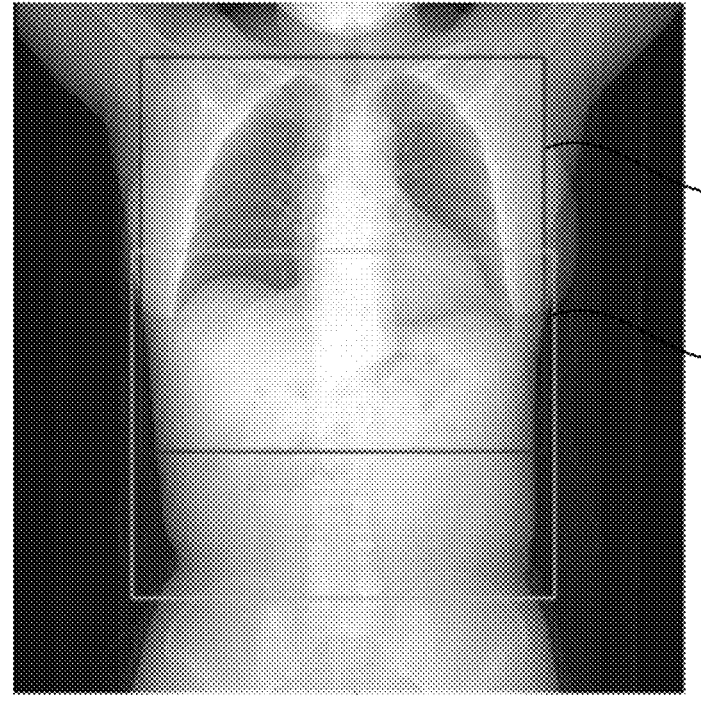
FIG. 5 is a schematic diagram illustrating positioning frame information in a scout image according to the embodiments of the present disclosure.

In some embodiments, the positioning model may be a region convolutional neural network (RCNN), a fastRCNN module, or a fasterRCNN model, etc. The positioning model may include a region generation sub-network and a target classification sub-network. The region generation sub-network may be a region proposal network (RPN) model. The region generation sub-network may be used to determine the positioning frame information in the scout image of the target object. For example, FIG. 5 is a schematic diagram illustrating positioning frame information in a scout image according to the embodiments of the present disclosure. FIG. 5 shows positioning frame 1 and positioning frame 2 identified and obtained by a region generation sub-network. A target classification sub-network may be connected with the region generation sub-network, and may be used to classify the portions corresponding to the positioning frame information output by the target classification sub-network, so as to obtain positioning frame information in a scout image and the corresponding portion information corresponding to the positioning frame information.

The positioning model may be obtained by training based on training scout images, information of the gold standard positioning frames, and the portion information corresponding to the information of the gold standard positioning frames. Each of the gold standard positioning frames may be in, from, or determined based on one of the training scout images and used for scanning. A portion corresponding to a gold standard positioning frame refers to a portion enclosed by a gold standard positioning frame. The training process of the positioning model may include an iterative process including iterations. Specifically, in each iteration, a training scout image may be input into the positioning model to be trained, prediction positioning frame information and classification information of prediction portions corresponding to the prediction frames may be obtained. A first loss function may be determined based on the information of the gold standard positioning frames and the prediction positioning frame information. A second loss function may be determined based on the portion information corresponding to the information of the gold standard positioning frames and the prediction portion classification information. Then a target loss function may be obtained based on the first loss function and the second loss function. Based on the target loss function, parameters of the positioning model are adjusted if a termination condition is not satisfied, and the above training process is iterated until the termination condition is satisfied (e.g., a convergence or a preset accuracy is reached), and the training is completed.

The first loss function may be a softmax loss, and the second loss function may be a smoothL1 loss. Correspondingly, the target loss function may be denoted as the following Equation (2):

$$L(\{p_i, t_i\}) = \frac{1}{N_{cls}} \sum_i L_{cls}(p_i, t_i) + \lambda \frac{1}{N_{reg}} \sum_i L_{reg}(p_i^*, t_i^*), \qquad (2)$$

where, $L(\{p_i, t_i\})$ indicates the target loss function, $p_i$ indicates the prediction positioning frame information, $p_i^*$ indicates the information of a gold standard positioning frame, $t_i$ indicates the prediction portion classification information, and $t_i^*$ indicates the portion information corresponding to the information of the gold standard positioning frame, $L_{cls}(p_i, t_i)$ indicates the first loss function, $L_{reg}(p_i^*, t_i^*)$ indicates the second loss function, a indicates a preset weight value, $N_{cls}$ indicates a mini-batch size of a training data set, and $N_{reg}$ indicates a number of candidate detection frames.

In some embodiments, a scanning protocol of the target object may be obtained, and the target positioning frame may be determined from each of the at least one of the positioning frames according to the scanning portion or scanning position in the scanning protocol.

In the technical solution provided by this embodiment, the scout image of the target object may be processed through the positioning model including the region generation sub-network and the target classification sub-network. The at least one positioning frame information and the portion classification information corresponding to the positioning frame information in the scout image are respectively obtained. By fully analyzing the scout image, a situation of missing any part may be avoided, and the comprehensiveness and accuracy of the positioning frame may be improved.

Figure 6:
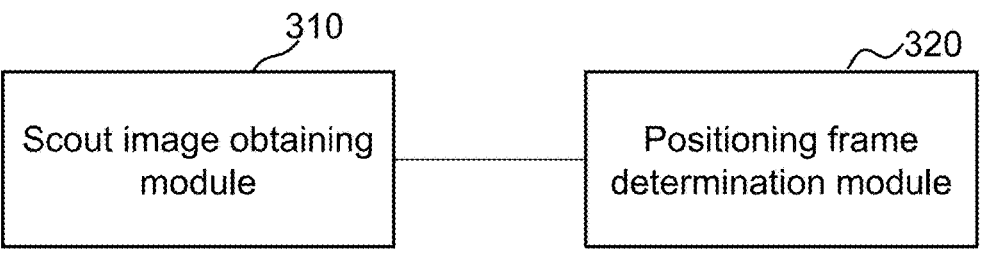
FIG. 6 is a schematic diagram illustrating a positioning device according to some embodiments of the present disclosure.

FIG. 6 is a schematic diagram illustrating a structure of a positioning device according to some embodiments of the present disclosure. The device may include a scout image obtaining module 310 and a positioning frame determination module 320.

The scout image obtaining module 310 may be configured to obtain a scout image of a target object.

The positioning frame determining module 320 may be configured to input the scout image of the target object into a positioning model, and determine a positioning frame in the scout image based on an output result of the positioning model. The positioning model may be obtained by training based on training scout images and information of the gold standard positioning frames. Each of the gold standard positioning frames may be in, from, or determined based on one of the training scout images and used for scanning.

In some embodiments, the positioning model may be a segmentation model.

In some embodiments, the positioning frame determining module 320 may be configured to: obtain a segmentation result output by the segmentation model; and determine an outline of a segmented region in the segmentation result as the positioning frame.

In some embodiments, the segmentation model may include an encoding module and a decoding module. The encoding module may include sequentially connected down-sampling network layers, and the decoding module may include sequentially connected up-sampling network layers. An end down-sampling network layer in the encoding module may be connected to an initial up-sampling network layer in the decoding module, and the down-sampling network layer and the up-sampling network layer in the encoding module and the decoding module of the same scale are horizontally connected.

In some embodiments, the device may further include a model training module configured to obtain the training scout images and the information of the gold standard positioning frames, and generate a gold standard mask region of each of the training scout images based on the information of one of the gold standard positioning frames corresponding to the training scout image; perform the following iterative training on the preliminary segmentation model until a prediction segmentation region output by the segmentation model meets a preset segmentation accuracy; the training scout image may be input into the preliminary segmentation model to obtain the prediction segmentation region, and a loss function may be determined based on the prediction segmentation region and the gold standard mask region. A network parameter adjustment may be performed on the preliminary segmentation model according to the loss function.

In some embodiments, the device may further include: a portion identification module configured to identify at least one portion included in the scout image after the obtaining of the scout image of the target object; and a model calling module configured to call the positioning model corresponding to each of the at least one portion based on the at least one portion. The positioning model corresponding to the at least one portion may be used to determine the positioning frame corresponding to each of the at least one portion.

In some embodiments, the positioning model may include a region generation sub-network and a target classification sub-network. The region generation sub-network may be used to generate the positioning frame corresponding to each of the at least one portion in the scout image, and the target classification sub-network may be used to determine scanning portion information corresponding to each of the at least one positioning frame.

In some embodiments, the device may further include: obtaining a scanning protocol of the target object; and determining a target positioning frame from each of at least one positioning frame corresponding to the at least one portion according to a scanning portion in the scanning protocol.

The above-mentioned products may perform the method provided by any embodiment of the present disclosure, and may have corresponding functional modules and beneficial effects for performing the method.

Figure 7:
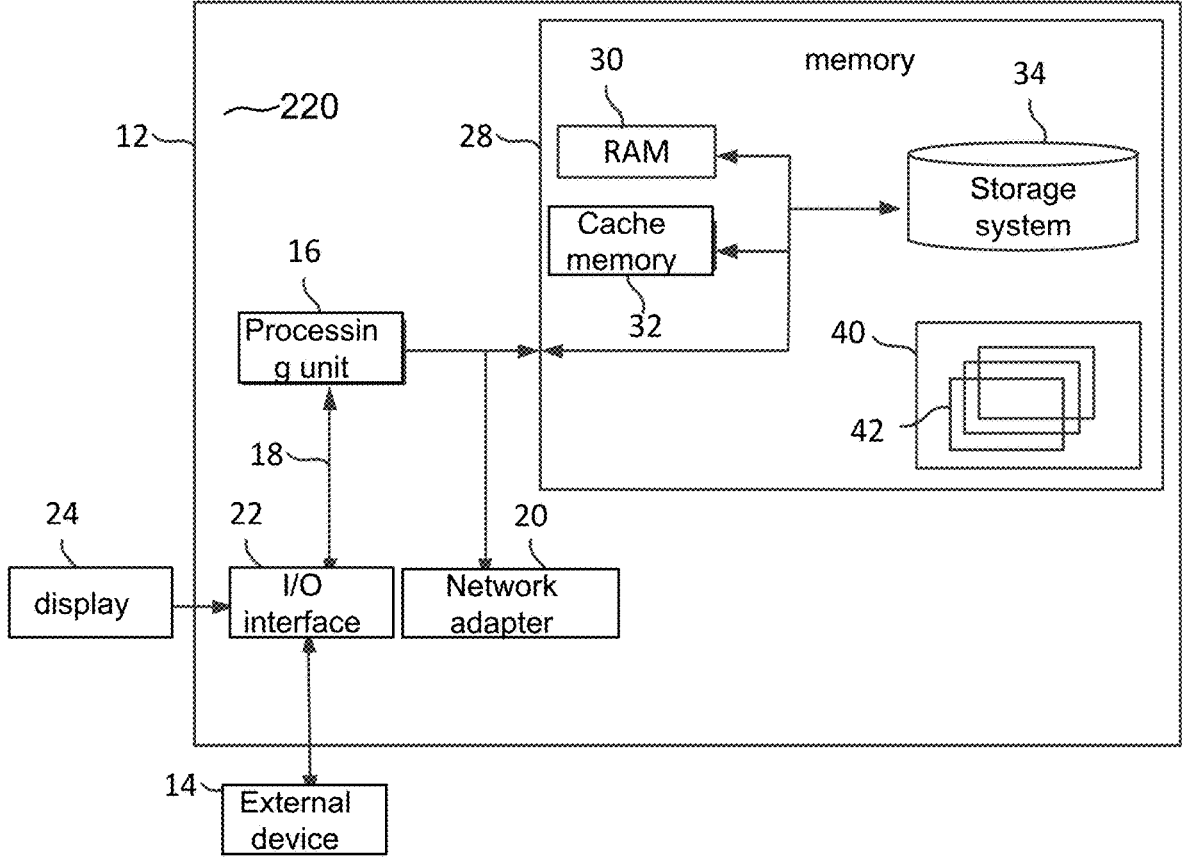
FIG. 7 is a schematic diagram illustrating an electronic device according to some embodiments of the present disclosure.

FIG. 7 is a schematic diagram illustrating a structure of an electronic device according to some embodiments of the present disclosure. The embodiment of the present disclosure provides services for the implementation of the processes of the above-mentioned embodiments of the present disclosure. The services may be configured with a model construction device in the present disclosure. FIG. 7 shows a block diagram of an exemplary electronic device 12 suitable for implementing embodiments of the present disclosure. The electronic device 12 shown in FIG. 7 is only an example, and should not limit the function and scope of the embodiments of the present disclosure.

As shown in FIG. 7, components of the electronic device 12 may include one or more processors or a processing unit 16, a system memory 28, a bus 18 connecting various system components (including the system memory 28 and the processing unit 16).

The bus 18 may represent one or more of several types of bus structures, including a memory bus or memory controller, a peripheral bus, a graphics acceleration port, a processor, or a local bus using any of the variety of bus structures. Examples of these architectures include, but are not limited to, an industry standard architecture (ISA) bus, a micro channel architecture (MAC) bus, an enhanced ISA bus, a video electronics standards association (VESA) local bus, and a peripheral component interconnect (PCI) bus.

The electronic device 12 may typically include a variety of computer system-readable media. These media may be any available media that can be accessed by electronic device 12, including volatile and nonvolatile media as well as removable and non-removable media.

The system memory 28 may include computer system-readable media in the form of volatile memory, such as a random access memory (RAM) 30 and/or a cache memory 32. The electronic device 12 may further include other removable/non-removable, volatile/nonvolatile computer system storage media. By way of example only, a storage system 34 may be used to read and write non-removable, non-volatile magnetic media (not shown in FIG. 7, commonly referred to as a "hard drive"). Although not shown in FIG. 7, disk drivers for reading and writing removable non-volatile disks (e.g. "floppy disks"), as well as compact discs (CDs) for reading and writing removable non-volatile (e.g., CD-ROM, DVD-ROM, or other optical media) removable non-volatile CDs may be provided. In these cases, each of the at least one driver may be connected to the bus 18 via one or more data media interfaces. The memory 28 may include at least one program product with a group (e.g., at least one) of program modules configured to perform the functions of various embodiments of the present disclosure.

A program/utility 40 with a group (at least one) of program modules 42 may be stored, for example, in memory 28. The program modules 42 may include an operating system, one or more application programs, other program modules, and program data, each, or some combination of which may be implemented in network environments. The program modules 42 may perform the functions and/or processes of the described embodiments of the present disclosure.

The electronic device 12 may further communicate with one or more external devices 14 (such as a keyboard, a pointing device, a display 24, etc.), one or more devices that enable a user to interact with the electronic device 12, and/or any device (e.g., a network card, a modem, etc.) that enables the electronic device 12 to communicate with one or more other computing devices. Such communication may be implemented through an input/output (I/O) interface 22. Moreover, the electronic device 12 may further communicate with one or more networks (such as a local region network (LAN), a wide region network (WAN), and/or a public network such as the Internet) through a network adapter 20. As shown in FIG. 7, the network adapter 20 may communicate with other modules of electronic device 12 via the bus 18. It should be appreciated that although not shown, other hardware and/or software modules may be used in conjunction with the electronic device 12, including but not limited to: a microcode, device drivers, redundant processing units, external disk drive arrays, redundant arrays of independent disks (EAID) systems, tape drives, and data backup storage systems, etc.

Through running the programs stored in the system memory 28, the processing unit 16 may perform various functional applications and data processing, such as implementing the process provided by some embodiment of the present disclosure.

The present disclosure also provides a non-transitory storage medium storing a computer program, the computer program including program instructions. When the program instructions are executed by a processor, the processor executes a method including obtaining a scout image of a target object, and inputting the scout image of the target object into a positioning model. The method may further include determining a positioning frame in the scout image based on an output result of the positioning model. The positioning model may be obtained by training based on training scout images and information of the gold standard positioning frames. Each of the gold standard positioning frames may be in, from, or determined based on one of the training scout images and used for scanning.

The computer storage medium in the embodiments of the present invention may use any combination of one or more computer-readable media. The computer-readable medium may be computer-readable signal media or computer-readable storage media. The computer-readable storage media may be, for example, but not limited to, an electrical, magnetic, optical, electromagnetic, infrared, or semiconductor system, device, or apparatus, or any combination thereof. More specific examples (a non-exhaustive list) of computer-readable storage media include: electrical connections with one or more leads, portable computer disks, hard disks, random access memory (RAM), read-only memory (ROM), erasable programmable read-only memory (EPROM or flash memory), optical fibers, portable compact disk read-only memories (CD-ROM), optical storage devices, magnetic storage devices, or any suitable combination of the above. In this document, the computer-readable storage medium may be any tangible medium that contains or stores the program that may be used by or in conjunction with an instruction execution system, apparatus, or device.

The present disclosure also provides a system. The system may include one or more processors; a memory configured to store one or more programs; when the one or more programs are executed by the one or more processors, the one or more processors may be made to implement the positioning process. The process may include obtaining a scout image of a target object; inputting the scout image of the target object into a positioning model; and determining a positioning frame in the scout image based on an output result of the positioning model, wherein the positioning model is obtained by training based on training scout images and information of the gold standard positioning frames, each of the gold standard positioning frames being from one of the training scout images and used for scanning. The system may perform a process as described elsewhere in the present disclosure.

A computer-readable signal medium may include a data signal carrying computer-readable program code in a baseband or as a portion of a carrier wave. Such data signal may be in many forms, including but not limited to an electromagnetic signal, an optical signal, or any suitable combination of the foregoing. The computer-readable signal medium may further be any computer-readable medium other than a computer-readable storage medium. The computer-readable medium can send, propagate, or transmit a program for use by or in conjunction with instruction execution systems, apparatus, or devices.

Program codes contained on the computer-readable medium may be transmitted using any appropriate medium, including but not limited to wireless, wireline, optical fiber cable, radio frequency (RF), etc., or any suitable combination of the foregoing.

The computer program code for performing the operations of the present disclosure may be written in one or more programming languages or combinations thereof, including object-oriented programming languages such as Java, Smalltalk, C++, and conventional procedural programming languages, such as the C language or similar programming languages. The program code may be performed entirely on the user's computer, partially on the user's computer, as a stand-alone software package, partially on the user's computer and partially on a remote computer or entirely on the remote computer or server. In a situation where a remote computer is involved, the remote computer may be connected to the user computer via any kind of network, including a LAN or a WAN, or the remote computer may be connected to an external computer (such as through an Internet connection using an Internet service provider).

Certainly, a storage medium containing computer-executable instructions is provided by the embodiments of the present disclosure. The computer-executable instructions may not be limited to the above-mentioned operations modes, and may further perform related operations in the positioning method provided by any embodiment of the present disclosure.

It should be noted that the above are only preferred embodiments and technical principles of the present disclosure. Those skilled in the art may understand that the present disclosure is not limited to the specific embodiments described herein, and that various obvious changes, rearrangements, and substitutions may be made by those skilled in the art without departing from the protection scope of the present disclosure. Therefore, although the present disclosure has been described in detail through the above embodiments, the present disclosure is not limited to the above embodiments, and may further include more other equivalent embodiments without departing from the concept of the present disclosure, and the scope of the present disclosure is determined by the scope of the appended claims.

What is claimed is:

1. A system, comprising:
   at least one storage medium including a set of instructions; and
   at least one processor configured to communicate with the at least one storage medium, wherein when executing the set of instructions, the at least one processor is configured to cause the system to perform operations including:
   obtaining a scout image of a target object;
   inputting the scout image of the target object into a positioning model; and
   determining a positioning frame in the scout image based on an output result of the positioning model, wherein the positioning model is obtained by training based on training scout images and information of gold standard positioning frames, each of the gold standard positioning frames being from one of the training scout images and used for scanning, the information of the gold standard positioning frames being determined according to current scan information for the target object.

2. The system of claim 1, wherein a historical positioning frame used for scanning a subject based on a scanning protocol that has at least one parameter same as a parameter of a scanning protocol for scanning the target object is designated as a gold standard positioning frame.

3. The system of claim 1, wherein the positioning model is a segmentation model, wherein the determining a positioning frame in the scout image based on an output result of the positioning model includes:

obtaining a segmentation result output by the segmentation model; and determining an outline of a segmented region in the segmentation result as the positioning frame.

4. The system of claim 3, wherein the segmentation model includes an encoding module and a decoding module, wherein the encoding module includes sequentially connected down-sampling network layers, and the decoding module includes sequentially connected up-sampling network layers, an end down-sampling network layer in the encoding module is connected to an initial up-sampling network layer in the decoding module, and the down-sampling network layer and the up-sampling network layer in the encoding module and the decoding module of the same scale are horizontally connected.

5. The system of claim 3, wherein a training process of the segmentation model includes:

obtaining the training scout images and the information of the gold standard positioning frames;

for one of the training scout images, generating a gold standard mask region of the training scout image based on the information of the gold standard positioning frame; and iteratively training, based on the training scout images and gold standard mask regions corresponding to the training scout images, a preliminary segmentation model to be trained, and obtaining the segmentation model.

6. The system of claim 1, wherein the operations further comprise:

identifying at least one portion of the target object in the scout image; and respectively calling, based on the at least one portion of the target object, the positioning model corresponding to each of the at least one portion of the target object, wherein the positioning model corresponding to one of the at least one portion of the target object is used to determine the positioning frame corresponding to the one of the at least one portion.

7. The system of claim 1, wherein the positioning model includes a region generation sub-network and a target classification sub-network, wherein the region generation sub-network is used to generate the positioning frame corresponding to each of the at least one portion in the scout image, and the target classification sub-network is used to determine scanning portion information corresponding to the positioning frame.

8. The system of claim 6, wherein the operations further comprise:

obtaining a scanning protocol of the target object; and determining a target positioning frame from each of at least one positioning frame corresponding to the at least one portion according to a target scanning portion in the scanning protocol.

9. The system of claim 1, wherein the operations further comprise:

determining a scanning region according to the positioning frame; and causing a scanning device to preform a scan on the target object based on the scanning region.

10. A method, comprising:

obtaining a scout image of a target object;

inputting the scout image of the target object into a positioning model; and determining a positioning frame in the scout image based on an output result of the positioning model, wherein the positioning model is obtained by training based on training scout images and information of gold standard positioning frames, each of the gold standard positioning frames being in one of the training scout images and used for scanning, the information of the gold standard positioning frames being determined according to current scan information for the target object.

11. The method of claim 10, wherein the positioning model includes a segmentation model, wherein the determining a positioning frame in the scout image based on an output result of the positioning model includes:

obtaining a segmentation result output by the segmentation model; and determining an outline of a segmented region in the segmentation result as the positioning frame.

12. The method of claim 11, wherein the segmentation model includes an encoding module and a decoding module, wherein the encoding module includes sequentially connected down-sampling network layers, and the decoding module includes sequentially connected up-sampling network layers, an end down-sampling network layer in the encoding module is connected to an initial up-sampling network layer in the decoding module, and the down-sampling network layer and the up-sampling network layer in the encoding module and the decoding module of the same scale are horizontally connected.

13. The method of claim 11, wherein a training process of the segmentation model comprises:

obtaining the training scout images and the information of the gold standard positioning frames;

for one of the training scout images, generating a gold standard mask region of the training scout image based on the information of one of the gold standard positioning frame corresponding to the training scout image; and iteratively training, based on the training scout images and gold standard mask regions corresponding to the training scout images, a preliminary segmentation model, and obtaining the segmentation model.

14. The method of claim 10, the method further comprising:

identifying at least one portion of the target object in the scout image; and respectively calling, based on the at least one portion of the target object, the positioning model corresponding to each of the at least one portion of the target object, wherein the positioning model corresponding to one of the at least one portion of the target object is used to determine the positioning frame corresponding to the one of the at least one portion of the target object.

15. The method of claim 10, wherein the positioning model includes a region generation sub-network and a target classification sub-network, wherein the region generation sub-network is used to generate the positioning frame corresponding to each of the at least one portion in the scout image, and the target classification sub-network is used to determine scanning portion information corresponding to the positioning frame.

16. The method of claim 15, further comprising:

obtaining a scanning protocol of the target object; and determining a target positioning frame from each of at least one positioning frame corresponding to the at least one portion according to a target scanning portion in the scanning protocol.

17. A non-transitory computer readable medium, comprising a set of instructions, wherein when executed by at least one processor, the set of instructions direct the at least one processor to perform acts of:

obtaining a scout image of a target object;

inputting the scout image of the target object into a positioning model; and determining a positioning frame in the scout image based on an output result of the positioning model, wherein the positioning model is obtained by training based on training scout images and information of gold standard positioning frames, each of the gold standard positioning frames being from one of the training scout images and used for scanning, the information of the gold standard positioning frames being determined according to current scan information for the target object.

18. The non-transitory computer readable medium of claim 17, wherein the positioning model includes a segmentation model, wherein the determining a positioning frame in the scout image based on an output result of the positioning model includes:

obtaining a segmentation result output by the segmentation model; and determining an outline of a segmented region in the segmentation result as the positioning frame.

19. The non-transitory computer readable medium of claim 18, wherein the segmentation model includes an encoding module and a decoding module, wherein the encoding module includes sequentially connected down-sampling network layers, and the decoding module includes sequentially connected up-sampling network layers, an end down-sampling network layer in the encoding module is connected to an initial up-sampling network layer in the decoding module, and the down-sampling network layer and the up-sampling network layer in the encoding module and the decoding module of the same scale are horizontally connected.

20. The non-transitory computer readable medium of claim 18, wherein a training process of the segmentation model comprises:

obtaining the training scout images and the information of the gold standard positioning frames;

for one of the training scout images, generating a gold standard mask region of the training scout image based on the information of one of the gold standard positioning frame corresponding to the training scout image; and iteratively training, based on the training scout images and gold standard mask regions corresponding to the training scout images, a preliminary segmentation model, and obtaining the segmentation model.

* * * * *